United States Patent
Searle et al.

(10) Patent No.: US 10,058,650 B2
(45) Date of Patent: Aug. 28, 2018

(54) NIGHTTIME BASAL DOSING DEVICE

(71) Applicant: Becton, Dickinson and Company, Franklin Lakes, NJ (US)

(72) Inventors: Gary M. Searle, Norfolk, MA (US); Charles G. Hwang, Wellesley, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 907 days.

(21) Appl. No.: 14/450,840

(22) Filed: Aug. 4, 2014

(65) Prior Publication Data

US 2014/0358119 A1 Dec. 4, 2014

Related U.S. Application Data

(62) Division of application No. 13/370,274, filed on Feb. 9, 2012, now Pat. No. 8,827,957.

(Continued)

(51) Int. Cl.
*A61M 5/142* (2006.01)
*A61M 5/145* (2006.01)
*A61M 5/158* (2006.01)

(52) U.S. Cl.
CPC ........ *A61M 5/145* (2013.01); *A61M 5/14248* (2013.01); *A61M 5/158* (2013.01);
(Continued)

(58) Field of Classification Search
CPC .............. A61M 5/14248; A61M 5/142; A61M 5/14244; A61M 5/1452; A61M 5/14586;
(Continued)

(56) References Cited

U.S. PATENT DOCUMENTS 5,776,103 A 7/1998 Kriesel et al.
5,858,005 A 1/1999 Kriesel
(Continued)

FOREIGN PATENT DOCUMENTS

JP H09504974 A 5/1997
JP 2001515371 A 9/2001
(Continued)

OTHER PUBLICATIONS

Notification of Transmittal of the International Search Report and the Written Opinion of the International Searching Authority, or the Declaration, dated Jun. 8, 2012, pp. 11.

*Primary Examiner* — Laura Bouchelle
(74) *Attorney, Agent, or Firm* — Dickinson Wright PLLC

(57) ABSTRACT

A basal hub for attaching to an infusion base is disclosed. The hub includes a fluid reservoir and pressure actuating device. A septum portion of the reservoir is configured to be opened by a flow cannula that is in fluid communication with an infusion cannula of the infusion base, when the basal hub is attached to the infusion base. The pressure actuating device applies pressure to the fluid reservoir, such that when the septum portion of the fluid reservoir is pierced by the by the flow cannula, liquid stored in the fluid reservoir is released from the fluid reservoir into the infusion cannula of the infusion base via the flow cannula. The basal hub is configured to deliver a basal dose of insulin during periods of inactivity, such as during sleep time.

10 Claims, 7 Drawing Sheets

Related U.S. Application Data

(60) Provisional application No. 61/441,278, filed on Feb. 9, 2011, provisional application No. 61/447,636, filed on Feb. 28, 2011.

(52) U.S. Cl.
CPC ............. *A61M 2005/14506* (2013.01); *A61M 2202/07* (2013.01); *A61M 2230/62* (2013.01)

(58) Field of Classification Search
CPC ........... A61M 2005/14268; A61M 2005/1587; A61M 2039/0205; A61M 2039/0208; A61M 2039/0229
See application file for complete search history.

(56) References Cited

U.S. PATENT DOCUMENTS

| | | | |
|---|---|---|---|
| 5,997,501 A | 12/1999 | Gross et al. | |
| 6,074,369 A | 6/2000 | Sage et al. | |
| 7,985,199 B2 | 7/2011 | Kornerup et al. | |
| 8,303,549 B2 | 11/2012 | Mejihede et al. | |
| 2004/0059316 A1* | 3/2004 | Smedegaard | A61M 5/14248 604/890.1 |
| 2007/0021717 A1 | 1/2007 | Gabe et al. | |
| 2007/0156033 A1 | 7/2007 | Causey, III et al. | |
| 2008/0215003 A1 | 9/2008 | Kornerup et al. | |
| 2008/0215006 A1 | 9/2008 | Thorkild | |
| 2009/0076453 A1 | 3/2009 | Mejlhede et al. | |
| 2009/0157003 A1 | 6/2009 | Jones et al. | |
| 2010/0057021 A1 | 3/2010 | Ishikura et al. | |
| 2011/0009813 A1* | 1/2011 | Rankers | A61B 5/15077 604/66 |
| 2011/0160696 A1* | 6/2011 | Hoss | A61M 39/02 604/506 |

FOREIGN PATENT DOCUMENTS

| | | |
|---|---|---|
| JP | 2010051702 A | 11/2010 |
| WO | WO-2006095701 A1 | 9/2006 |

\* cited by examiner

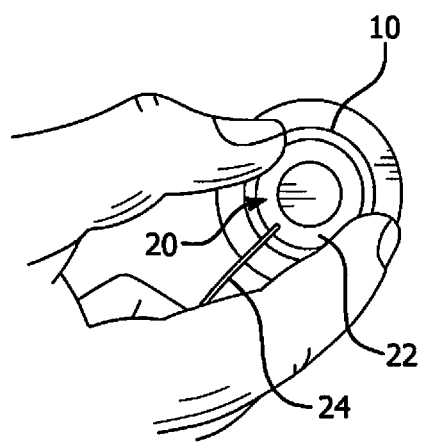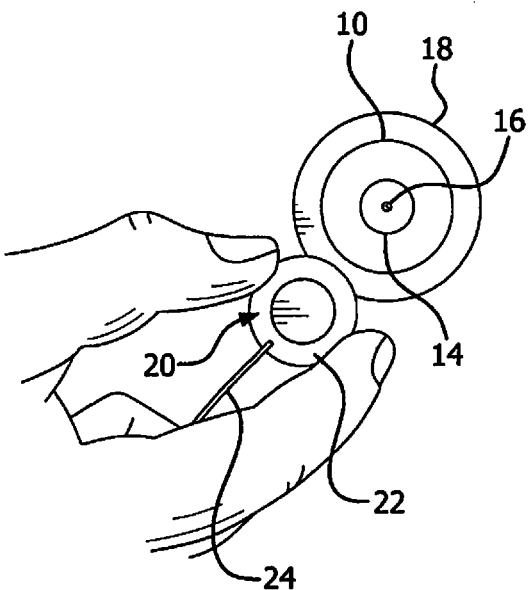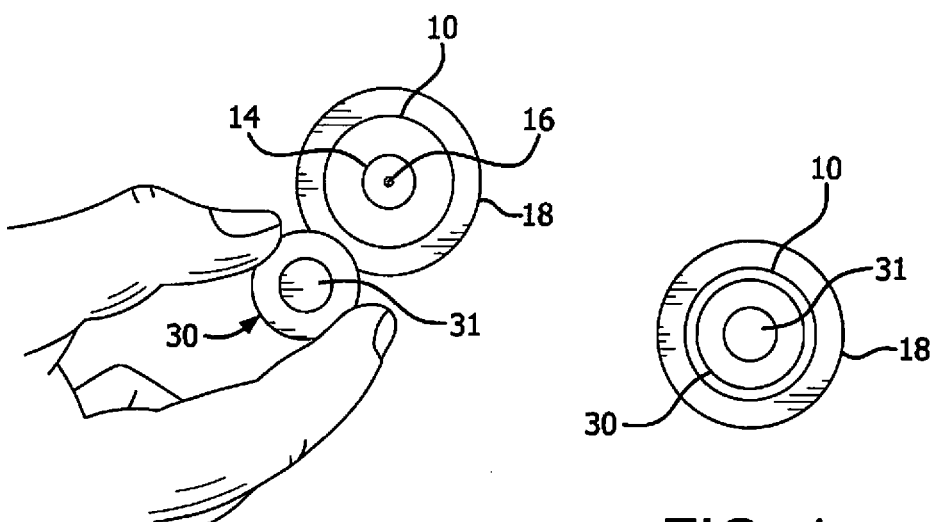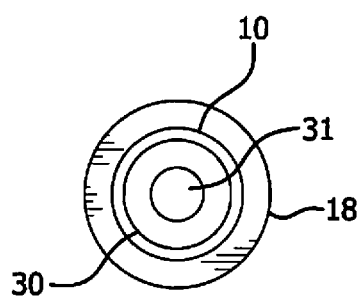
FIG. 1
FIG. 2
FIG. 3
FIG. 4

NIGHTTIME BASAL DOSING DEVICE

CROSS-REFERENCE TO RELATED APPLICATION

This application is a division of U.S. patent application Ser. No. 13/370,274, filed on Feb. 9, 2012, which is incorporated by reference in its entirety. This application also claims the benefit under 35 U.S.C. § 119(e) of U.S. Provisional Application Nos. 61/441,278, filed on Feb. 9, 2011, and 61/447,636, filed on Feb. 28, 2011, the disclosures of both of said applications also being incorporated herein by reference in their entirety.

FIELD OF THE INVENTION

The present invention relates to components and elements of infusion systems, and more specifically to an infusion system that can be used for basal delivery of insulin or other liquid medicament during periods of rest without the need for permanent attachment of a separate tubeset and pump device.

BACKGROUND OF THE INVENTION

A large number of people with diabetes use some form of daily insulin therapy to maintain close control of their glucose levels. Currently, there are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the use of an insulin pump. Although the initial cost of the pump can be significant, the overwhelming majority of patients who have used pumps prefer to remain with pumps. This is because infusion pumps, although more complex than syringes and pens, offer the advantages of continuous infusion of insulin, precision dosing, and programmable delivery schedules. This results in closer blood glucose control, which can result in improved health outcomes for the patients.

The use of an infusion pump requires the use of a disposable component, typically referred to as an infusion set, line set, extension set or pump set, which conveys the insulin from a reservoir within the pump into the skin of the user. An infusion set typically consists of a pump connector, a length of tubing, and a hub or base from which an infusion cannula (i.e., an infusion needle or a flexible catheter) extends. The hub or base has an adhesive which retains the base on the skin surface during use, which may be applied to the skin manually or with the aid of a manual or automatic insertion device.

However, there are problems associated with the delivery of insulin by such devices during sleep. During sleep, people tend to move and such movement can result in accidental disconnection of the line set, removal of the infusion cannula, or tugging of the line set that can result in tunneling or leakage at the infusion site. Tunneling can occur when an infusion cannula that has been inserted into a user leaks insulin along the outer walls of the tubing of the infusion cannula, back to the skin, usually after a large bolus. Since many components are attached to the user of such devices, this further adds to the level of discomfort to the user, reducing the comfort level of the user during periods of rest when discomfort should be minimized.

In addition, during periods of rest, such as during sleep at night, a diabetic patient is subject to different conditions than during times of activity, such as during the day. During sleep time, since the patient does not eat, the level of insulin required (basal dose) is nearly constant and substantially reduced as compared to the insulin requirement (bolus dose) at meal times or during active times during the day.

Accordingly, a need exists for a device that can deliver basal dose medication to the subcutaneous or intradermal skin layer, during times of rest, while maintaining a high degree of comfort to the user by eliminating unnecessary components that contribute to user discomfort.

SUMMARY OF THE INVENTION

An object of the present invention is to provide a relatively small basal delivery system that is not connected to a tubeset or pump when it is used during times of rest or when the patient is disconnected from the infusion pump for extended periods.

Another object of the present invention is to provide a pressurized fluid reservoir having a septum that allows release of fluid when the septum is opened.

Another object of the present invention is to provide a spring actuated device or mechanical element to apply pressure on the fluid reservoir.

Another object of the present invention is to provide an elastic or flexible membrane attached to the cover of the device to form the pressurized fluid reservoir.

Another object of the present invention is to provide a flow cannula that is secured on an infusion hub connector or adapter that is configured to open the integral septum.

These and other objects are substantially achieved by providing a basal hub configured to attach to an infusion base. The basal hub includes a cover, a fluid reservoir within the cover, and a septum connected to the fluid reservoir. The septum is configured to be opened by a flow cannula of the infusion base, and the flow cannula is in fluid communication with an infusion cannula of the infusion base. The septum is positioned on the fluid reservoir, and a pressure actuating device applies pressure to the fluid reservoir, such that when the septum of the basal hub is opened by the flow cannula, liquid stored in the fluid reservoir is released from the fluid reservoir into the infusion cannula of the infusion base via the flow cannula and into the infusion cannula. The basal hub maintains a high degree of comfort to the user by allowing the user to receive basal therapy without being connected to an infusion pump.

BRIEF DESCRIPTION OF THE DRAWINGS

The various objects, advantages and novel features of exemplary embodiments of the present invention will be more readily appreciated from the following detailed description when read in conjunction with the appended drawings, in which:

FIG. 1 is a plan view of an exemplary infusion set in which an exemplary line set is attached to an exemplary infusion base;

FIG. 2 is a plan view of the device of FIG. 1 after the line set has been disconnected and removed from the infusion base;

FIG. 3 is a plan view of an exemplary basal hub of the present invention being aligned for attachment to the infusion base of FIG. 2;

FIG. 4 is a plan view of the basal hub of FIG. 3 attached to the infusion base of FIG. 3;

DETAILED DESCRIPTION OF THE EXEMPLARY EMBODIMENTS

The exemplary embodiments of the present invention described below provide a novel means for basal delivery of insulin or other medicament to the subcutaneous or intradermal layer of skin while the user is not connected to a standard insulin pump or other reservoir.

An exemplary embodiment of the present invention includes a basal hub that is similar in size and shape to a sterile or sanitary hub that is commonly attached to an infusion base when the line set or extension set is disconnected from the infusion base, to protect the infusion base that is attached to a diabetic patient from contamination.

The basal hub generally incorporates a flexible reservoir that is preloaded by a spring or other mechanical element or device that applies pressure to the flexible reservoir. Also included is a septum in the reservoir positioned to engage with a flow cannula located in or provided on the infusion base, such that when the basal hub is attached to the infusion base and the flow cannula pierces the septum, insulin from the reservoir will flow into the infusion site. The flow cannula and spring are sized and configured to provide a specific flow rate that corresponds with the diabetic patient's nighttime basal requirement, reflecting the diabetic patient's weight, metabolism and other factors. The size of the reservoir can be varied for customized use, within the limits of the size of the basal hub.

Currently marketed infusion sets (not shown) may include a sanitary hub/protective hub that covers the connection site on the infusion base during brief periods when the line set or extension set is disconnected. For instance, when the patient is about to swim or take a shower, the line set is preferably disconnected from the infusion base, and a protective or sanitary hub is placed on the infusion base, in lieu of the line set, in order to protect the fluid interface from contamination.

As illustrated in FIGS. 1-4, the infusion set 20 and the basal hub 30 are similar in size to a conventional infusion set and its sanitary hub, respectively. However, unlike the conventional protective hub, the basal hub 30 also incorporates a reservoir or pressurized bladder 34 that can infuse insulin at a preset basal rate during periods of inactivity including sleep, without being connected to a separate line set or pump.

Prior to sleeping, the basal hub 30 attaches to the infusion base 10, in a manner similar to that of the extension set 20 or line set, after the extension set 20 has been removed from the infusion base 10. In contrast, in a conventional infusion set, the tube set remains connected to its pump (not shown) while the diabetic patient sleeps, so that the patient receives his/her nighttime basal dose from the pump. However, the presence of the pump and tube set creates complications for the diabetic patient while sleeping, since, as the patient moves during sleep, line set tugging or unintended disconnection can occur.

Figure 6A:
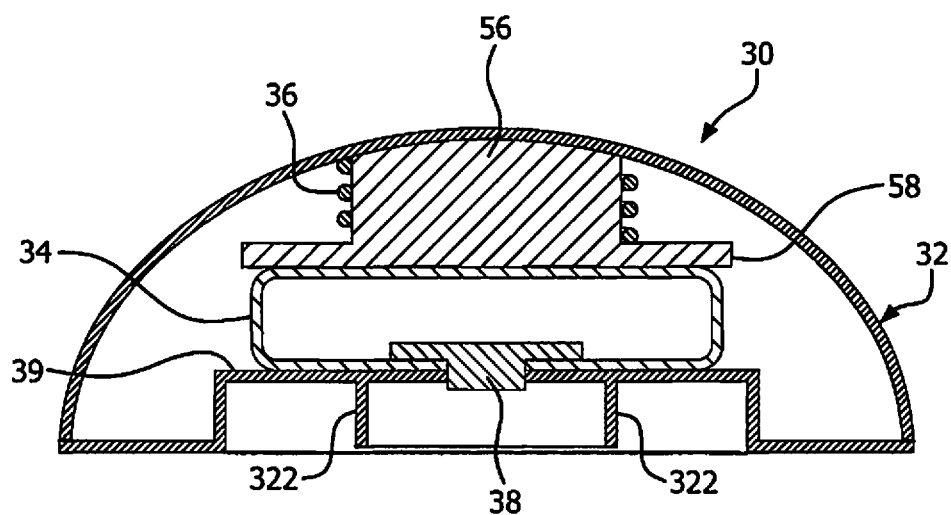
FIG. 6A is a cross-sectional view of the exemplary basal hub device of FIG. 3 in accordance with an embodiment of the present invention.

During sleep, since only basal dosing is required, as opposed to a bolus dose before a meal, for a diabetic patient, a small hub, similar in size to a protective hub or sanitary hub that can be attached and detached in a manner similar to a line set, is provided and configured with a pre-loaded flexible reservoir or bladder 34, illustrated in FIG. 6A, containing a quantity of insulin that is released at a predetermined rate during sleep without the need to connect the basal hub 30 to a tube set during use, that in turn connects to a pump containing insulin. The absence of an external tube set and additional components, such as a pump, provides clear advantages over conventional infusion sets when the diabetic patient is sleeping or resting for a period of time.

FIG. 1 illustrates a line set 20 attached to the infusion base 10 (as shown in FIG. 2). An infusion cannula 15, illustrated in FIG. 5, is attached to the infusion base 10. The infusion cannula 15 penetrates the skin of the diabetic patient during use, with initial penetration being facilitated by a separate introducer needle (not shown) as is known in the art. A rigid metal needle may be used in place of the infusion cannula 15, in which case a separate introducer needle is not required. Thereafter, the adhesive pad 18, attached to the infusion base 10, adheres to the skin of the patient to secure the infusion base 10 and the infusion cannula 15 on the patient's skin. The housing or hub 22 of the extension set 20 is connected to a tube set 24, which is then connected to a pump (not shown) containing a reservoir of insulin or other liquid medication.

FIG. 2 illustrates detachment of the extension set 20 from the infusion base 10. The infusion base 10 includes a flow cannula 16 at an upper surface thereof. The flow cannula 16 and the infusion cannula 15 are shown in greater detail in FIGS. 5B and 6B.

Figure 5A:
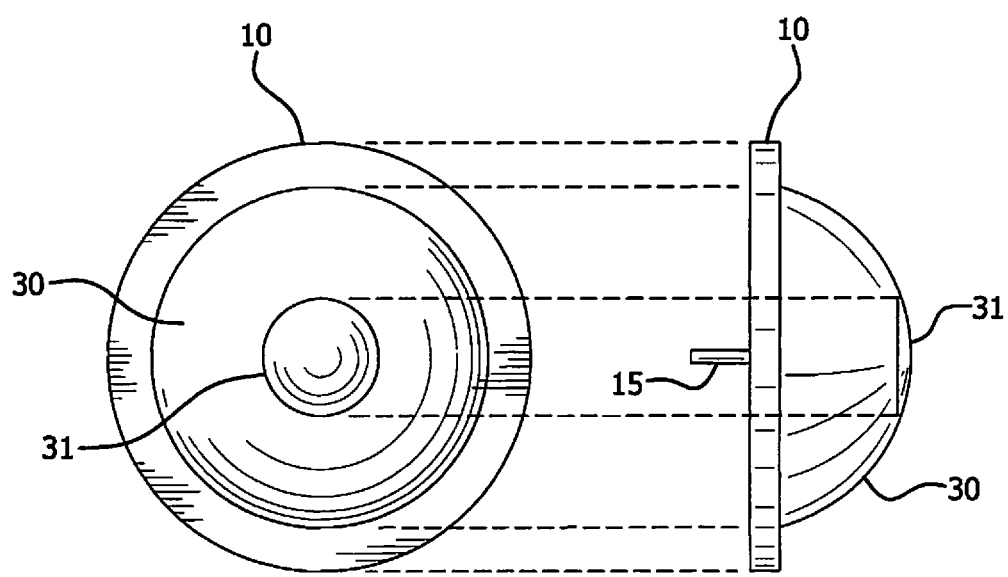
FIG. 5A includes a plan view and a side view of the basal hub of FIG. 3 shown attached to the infusion base of FIG. 2.

FIGS. 3 and 4 illustrate the attachment of the inventive basal hub 30 on the infusion base 10 after removal of the extension set 20. The basal hub 30 may have a marking 31, such as a color spot, for better visual identification, or a see-through cover to reveal the internal components. FIG. 5A further illustrates the attachment of the basal hub 30 to the infusion base 10.

Figure 5B:
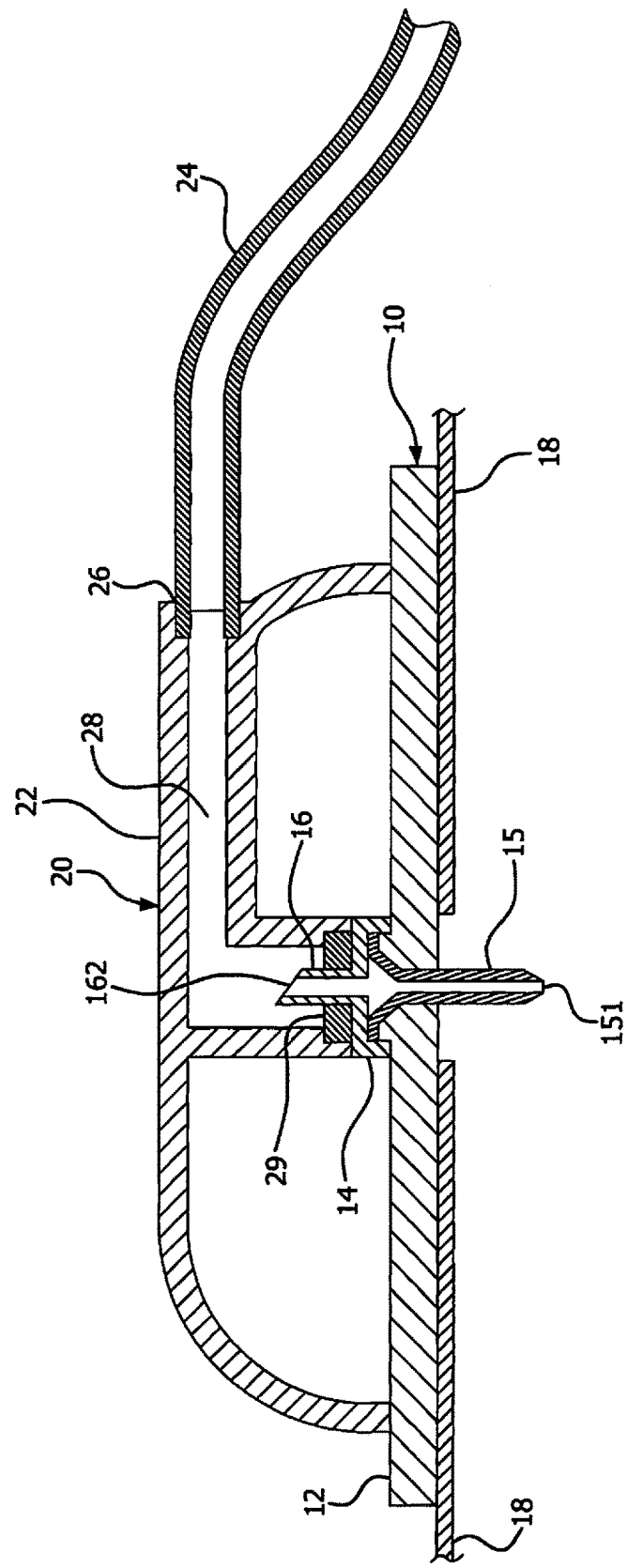
FIG. 5B is a cross-sectional view of the line set device of FIG. 2 attached to the infusion base of FIG. 2.

FIG. 5B illustrates a cross-sectional view of the line set 20 attached to infusion base 10. The infusion base 10 includes a main base portion 12, an infusion cannula 15 extending through the main base portion 12, and an infusion hub connector or adapter 14 having a flow cannula 16. As illustrated in FIG. 5B, the flow cannula 16 and adapter 14 can be made as a single unit. A fluid path is formed from the opening 162 of the flow cannula 16 to the distal opening 151 of the infusion cannula 15. An adhesive pad 18 is attached to an outer surface of the main base portion 12 and is also attached to the skin of the diabetic patient.

The line set 20 functions to deliver insulin into the flow cannula 16 of the infusion base 10. As illustrated in FIG. 5B, the line set 20 includes a housing or hub 22, tube set 24 attached to the hub 22 at the hub port 26, and septum 29. The tube set 24 is connected to a pump (not shown) that delivers insulin into the tube set 24. A fluid path 28 exists between the tube set 24 and the septum 29. The septum 29 is closed when the line set 20 is detached from the infusion base 10. The septum 29 is positioned on the hub 22 such that when the line set 20 is attached to the infusion base 10, as illustrated in FIG. 5B, the flow cannula 16 of the infusion base 10 pierces the septum 29. After the septum 29 is pierced by the flow cannula 16, insulin flows from the pump (not shown) into the tube set 24, through the flow path 28, into the flow cannula 16 via its open tip 162, and into the infusion cannula 15 to deliver insulin into the patient through the distal opening 151 of the infusion cannula 15. This is the preferred way to deliver insulin when the diabetic patient is active and requiring different levels of insulin, such as at meal times (requiring a bolus dose) or during active times of the day. However, during sleep time, since the patient is inactive and does not intake any food, the required level of insulin (basal dose) is greatly reduced and relatively constant in comparison to the insulin requirements during the day or during active times.

The basal hub 30 illustrated in FIG. 6A can replace the line set 20 during sleep time of the diabetic patient. The basal hub 30 is a self-contained unit that is not connected to an external device, such as the tube set 24 and external pump, for receiving and transferring insulin to the patient, unlike the line set 20.

Before sleeping, the patient disconnects the line set 20 from the infusion base 10. When the line set 20 is detached from the infusion base 10, the flow cannula 16 is withdrawn from the septum 29 of the line set 20 and the septum 29 self-closes the opening pierced by the flow cannula 16, to prevent pathogens or foreign matter entering the fluid path 28 of the line set 20. After the line set 20 has been removed from infusion base 10, the infusion base 10 can receive a basal hub 30.

As illustrated in FIG. 6A, the basal hub 30 includes an outer cover or housing 32 that is relatively rigid, in order to protect the structures within the basal hub 30. The basal hub 30 includes a pre-loaded compression spring 36 that pressurizes a sealed, flexible reservoir or bladder 34. The spring 36 encircles a cylindrical post 56 and the spring 36 is compressed between the housing 32 and a plate 58 that is part of the post 56. The spring 36 presses on the plate 58 and pressurizes the bladder 34 which is positioned between the plate 58 and a septum 38 and a lower portion 39 of the housing 32. The lower portion 39 of the housing 32 can be a separate piece that is assembled with the rest of the housing 32 and then attached together. The septum 38 can be made integral with the bladder 34. With reference to FIG. 6A, the cylindrical post 56 can be a splined shaft, with mating spline features of the splined shaft molded to the cover or housing 32. The cylindrical post 56 is slideable on the mating spline features of the housing 32, with the spring 36 tensioned between the cover 32 and the plate 58 of the cylindrical post 56. This arrangement provides proper alignment of the cylindrical post 56 with the cover or housing 32, and also provides alignment for the spring 36 as the pressurized bladder 34 releases its contents.

Figure 6B:
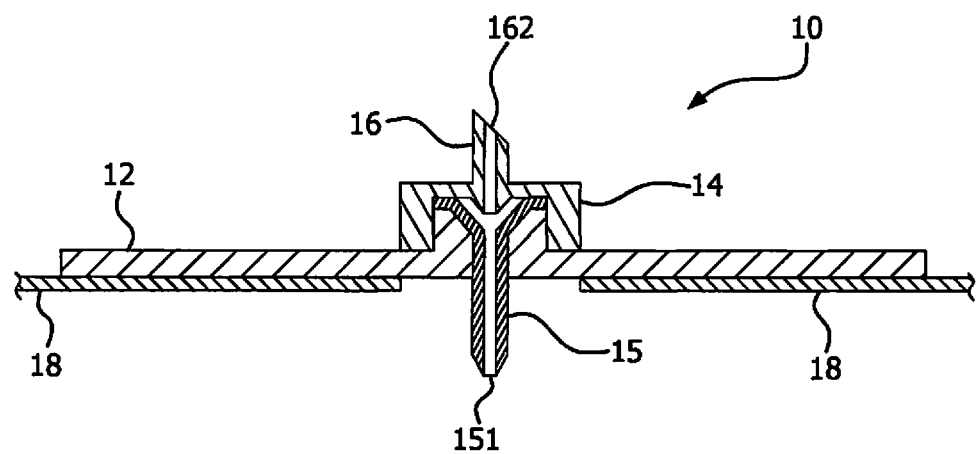
FIG. 6B is a cross-sectional view of an exemplary infusion base with a flow cannula that is aligned to penetrate a septum of the device of FIG. 6A, the infusion base being adapted to receive the exemplary device of FIG. 6A.

When the basal hub 30 illustrated in FIG. 6A is connected to the infusion base 10 illustrated in FIG. 6B, the flow cannula 16 of the adapter 14 pierces the septum 38 of the basal hub 30, upon which event the spring force of the spring 36 and the inner diameter and length of flow cannula 16 determines the basal infusion rate through the infusion cannula 15, as insulin from the bladder 36 enters flow cannula 16 through its open tip 162 and exits through the distal opening 151 of the infusion cannula 15. Both the infusion rate of insulin and the reservoir volume, as well as the diameter and length of the flow cannula, are preset to the specific requirements of the diabetic patient, according to the patient's weight, metabolism and other factors. The basal hub 30 can be prefilled with insulin in a variety of different configurations with different combinations of insulin capacity and flow rate to suit different users. Guide element 322 can be cylindrical and incorporated into the housing 32 to act as a guide, such that the adapter 14 of the infusion base 10 is positioned inside the cylindrical guide element 322 to align the flow cannula 16 to properly penetrate the septum 38.

The reservoir 34 may be flexible but it can also be non-flexible, as in a cylinder and piston arrangement, in which case the spring 36 or similar mechanical element acts on the reservoir as a piston to release the insulin via the septum 38 that has been opened or pierced by the flow cannula 16 when the basal hub 30 is attached to the infusion base 10.

As illustrated in FIG. 6B, there is fluid communication between the flow cannula 16 and the infusion cannula 15. Once the flow cannula 16 pierces the septum 38 that is integral with the bladder 34, upon attachment of the basal hub 30 to the infusion base 10, a fluid path is created from the reservoir 34, through the flow cannula 16, and to the infusion cannula 15, so that insulin in the reservoir is delivered to the patient at the desired basal rate.

Figure 7A:
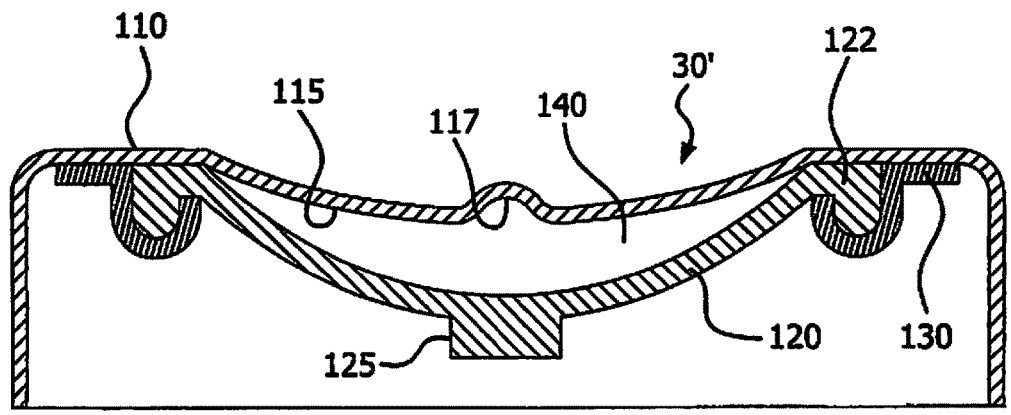
FIG. 7A is cross-sectional view of another exemplary basal hub device in accordance with another embodiment of the present invention.

FIG. 7A illustrates another basal hub embodiment of the present invention. Basal hub 30' of FIG. 7A provides the intended function of the basal hub 30 of FIG. 6A with a fewer number of components and is generally more basic or rugged in design. The basal hub 30' of FIG. 7A has been simplified to include three basic components, namely a substantially rigid cover 110, a flexible and resilient membrane 120 with a septum 125 that can be molded into the flexible and resilient membrane 120, and a retention or retaining ring 130. The fluid reservoir 140 is formed between the cover 110 and the flexible membrane 120, as illustrated in FIG. 7A.

The flexible membrane 120 is stretched over the domed surface 115 of the cover 110 and is retained in place by the retaining ring 130, with the retaining ring 130 capturing a bead 122 of the flexible membrane 120, as illustrated in FIG. 7A, to contain the fluid reservoir 140. As the fluid reservoir 140 is filled under pressure with insulin or other medication, the flexible membrane 140 stretches away from the cover, as illustrated in FIG. 7A to accommodate the insulin or other medication. The insulin can be filled in the fluid reservoir 140 through the septum 125 or through an opening (not shown) in the cover 110 that is closed after the insulin has filled the fluid reservoir 140. The tension of the flexible membrane 120 provides the infusion pressure, as illustrated in FIG. 7A, in place of a spring 36 or similar mechanical element. The retaining ring 130 can be directly attached to the cover 110 by adhesive, ultrasonic welding or other joining methods. The basal hub 30' of FIG. 7A can be attached to the infusion base 10' of FIG. 7B in a manner similar to the attachment of the basal hub 30 of FIG. 6A on the infusion base 10 of FIG. 6. Guide elements can be provided on the basal hub 30' and/or the infusion base 10' to properly align the elements so that upon attachment of the basal hub 30' to the infusion base 10', the flow cannula 16' penetrates the septum 125 so that insulin in the fluid reservoir 140 flows into the flow cannula 16' via the open tip 162' and into the infusion cannula 15 to administer the insulin to the diabetic patient. The rate of flow of the insulin from the fluid reservoir 140 can be determined by several factors, including the tension force of the flexible membrane 140, the diameter of the open tip 162' of the flow cannula, the diameter of the distal opening 151, the lengths of the flow cannula 16' and infusion cannula 15,and so on.

Figure 7B:
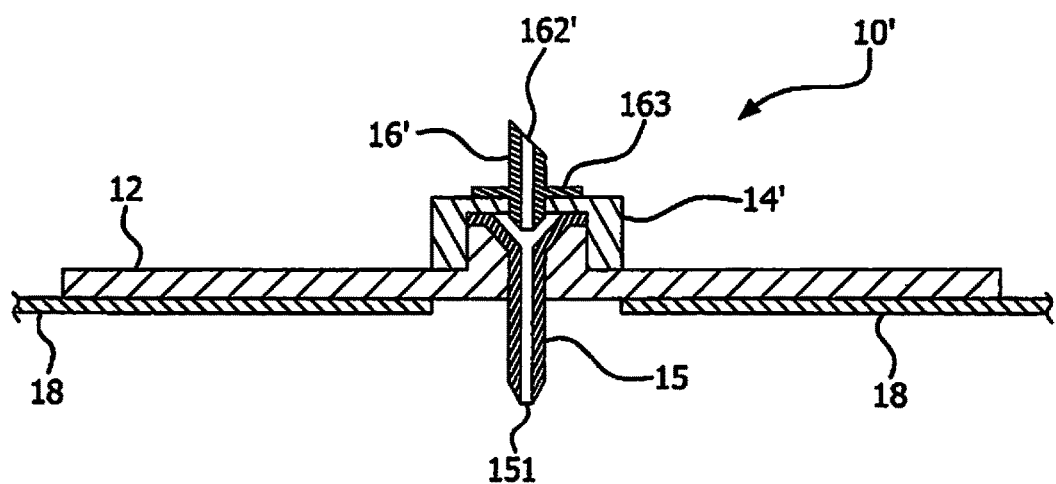
FIG. 7B is a cross-sectional view of another exemplary infusion base with a flow cannula that is aligned to penetrate a septum of the basal hub device of FIG. 7A, the infusion base being adapted to receive the basal hub device of FIG. 7A.

The infusion base 10' of FIG. 7B is similar to the infusion base 10 of FIG. 6B, but the cannula 16' is not part of the adapter 14'. The cannula 16' includes a flanged base 163 that positions and rests the cannula 16' on the adapter 14', as illustrated in FIG. 7B. One or more elements of the infusion base 10, 10', including the flow cannula 16, 16', adapter 14, 14', infusion cannula 15, and the main base portion 12 can be made together (e.g. by injection molding) or separately and assembled to form the infusion base 10, 10'. In still another embodiment, utilizing a steel cannula, the flow cannula and the infusion cannula could be combined into a single element, with or without an adapter to secure the element to the main base. The flanged feature or flanged base 163 at the infusion cannula 16' can be replaced with a bulged portion in the combined single element, which can be produced in a forming process similar to the process used to form the head on a capacitor pin.

As illustrated in FIG. 7A, the domed surface 115 of the cover 110 includes an indent 117 which allows the cannula 16' to draw fluid from the fluid reservoir 140, as the fluid reservoir 140 becomes depletion. Upon attachment of the basal hub 30' to the infusion base 10', the flow cannula 16' penetrates close to the indent 117, and as the tension of the resilient membrane 120 is released, the resilient membrane 120 is drawn toward the domed surface 115 of the cover 110, and the remaining amount of the fluid in the fluid reservoir 140 is directed to the indent 117 to be drawn into the flow cannula 16'. The embodiment of FIGS. 8A and 8B illustrate similar use of an indent.

Figure 8A:
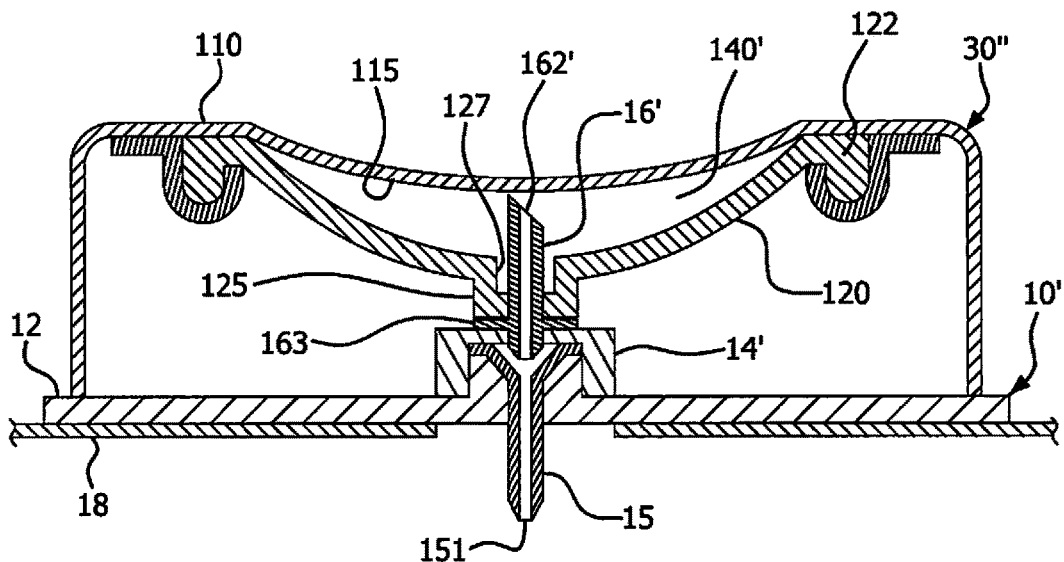
FIG. 8A is cross-sectional view of another exemplary basal hub device in accordance with another embodiment of the present invention.

FIG. 8A illustrates another exemplary basal hub 30''' that is similar to the basal hub 30' of FIG. 7A, but the basal hub 30''' includes an indent 127 at its septum 125. FIG. 8A shows the basal hub 30''' attached to the infusion base 10' when the flow cannula 16' initially penetrates the septum 163. This is the initial state of the fluid reservoir 140'. Thereafter, the fluid reservoir 140' becomes gradually depleted as insulin flows from the fluid reservoir 140' into the flow cannula 16' and exits through the infusion cannula 15.

Figure 8B:
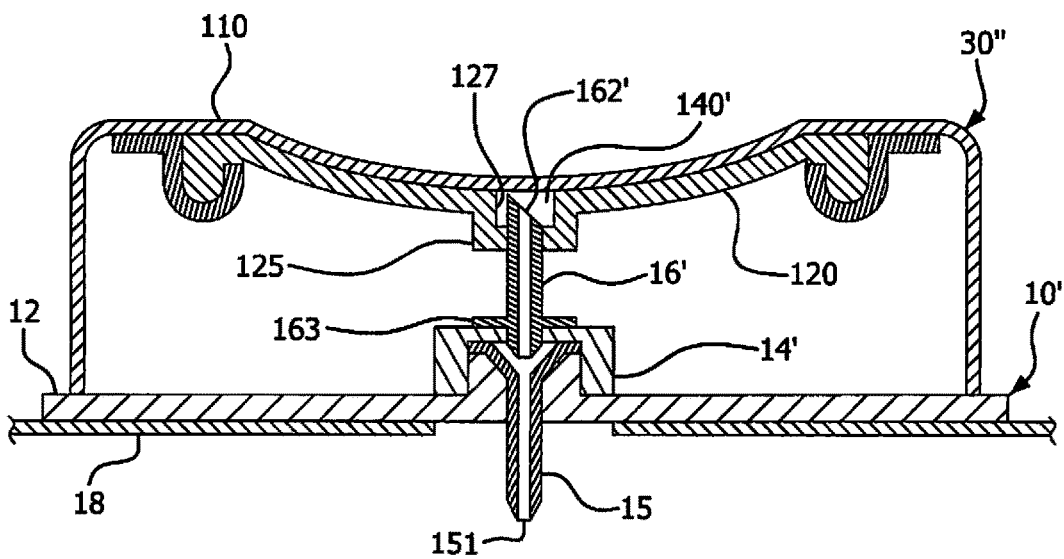
FIG. 8B is a cross-sectional view of another exemplary infusion base with a flow cannula that is aligned to penetrate a septum of the basal hub device of FIG. 8A, the infusion base being adapted to receive the basal hub device of FIG. 8A.

FIG. 8B illustrates the state when the fluid reservoir 140' is fully depleted, with the remaining insulin being directed into the indent 127 formed on the septum of the resilient membrane 120. Due to the indent 127, most of the fluid in the fluid reservoir 140' can be administered to the diabetic patient.

Figure 9A:
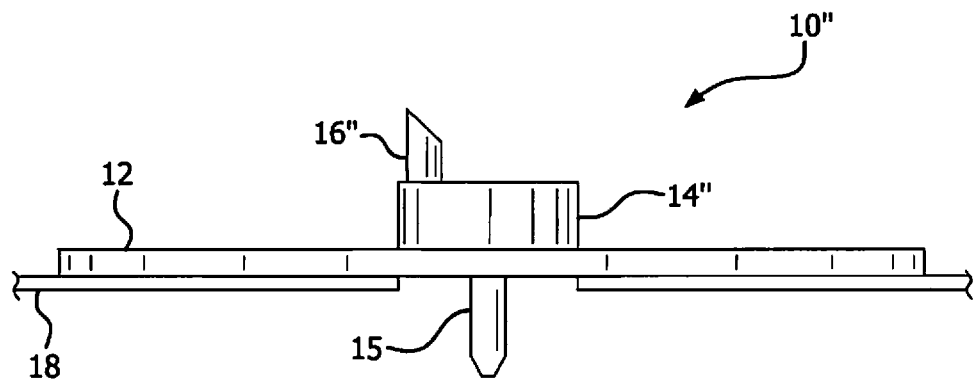
FIG. 9A is side view of another exemplary infusion base.
Figure 9B:
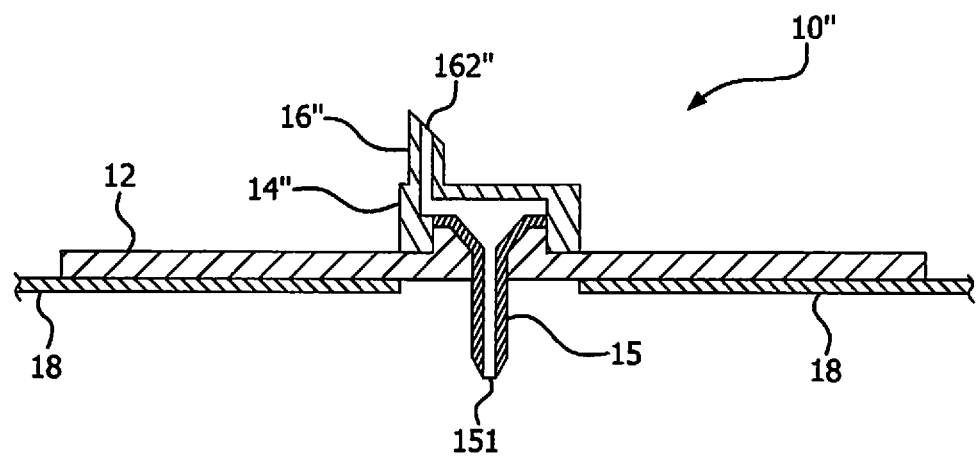
FIG. 9B is a cross-sectional view of the infusion base of FIG. 9A.

FIGS. 9A and 9B illustrate another exemplary infusion set 10'' designed to better accommodate the introducer needle (not shown) that typically extends into the infusion cannula 15 to permit insertion of the introducer needle and infusion cannula 15 into the patient, without inserting the introducer needle into the flow cannula 16''. Typically, the introducer needle is removed and a septum (not shown) closes the exit point of the introducer needle in the infusion base 10''. In FIGS. 9A and 9B, however, an alternative design is shown in which the flow cannula 16'' is included in the infusion base 10'' and is displaced laterally away from the site of the introducer needle. A fluid path is formed through the adapter 14'' from the open tip 162'' of the flow cannula 16'' to the distal tip 151 of the infusion cannula 15 after the introducer needle has been removed from the infusion base 10''.

The basal hub 30, 30', 30'' can be modified for use with the infusion set 10'' by repositioning the septum 38, 125 to be opened by the flow cannula 16'' when the basal hub 30, 30', 30'' is attached on the infusion base 10'' of FIGS. 9A and 9B. Alternatively, as is the case in the preceding embodiment, the introducer needle can pass through both the flow cannula and the infusion cannula.

The basal hub 30, 30', 30'' is intended to be used in conjunction with the line set 20 of FIG. 5B. The basal hub 30, 30', 30'' can also be modified or adapted for use with commercially available line sets.

Since the line set 20 and pump (not shown) is disconnected before the usage of the basal hub 30, 30', 30'', this can result in a loss of insulin infusion data for the patient. At present, insulin infusion pumps generally capture the infusion profile of the entire 24-hour day, and this record can be downloaded to a patient's health care provider for analysis.

Although the pump controller can be modified to allow the user to enter or record his/her total nighttime basal requirement, another embodiment of the present invention allows the infusion profile to be captured during sleep. This can be done by making the basal hub 30, 30', 30'' an integral part of the infusion set. In this embodiment, in preparation for sleeping, the patient disconnects the hub 22 of the line set 20 from the infusion base 10, implements a command from the infusion pump controller to fill the device reservoir 34, 140, 140' with the quantity of insulin required for the nighttime basal dose, disconnects the line set 20, and connects the basal hub 30, 30', 30'' to the infusion base 10, 10' 10''. With this process, the total nighttime insulin dose is recorded as a bolus dose by the infusion pump without requiring any modification to the pump controller.

The reservoir 34, 140, 140' is designed to stop the outflow of its liquid contents when disconnected from the infusion base 10, as the septum 38, 125 self-closes after the flow cannula 16, 16', 16'' is withdrawn from the septum 38, 125. Reconnection of the basal hub 30, 30', 30'' to the infusion base 10, 10', 10'' results in insulin flow from the reservoir 34, 140, 140' to the infusion site.

The infusion base 10, 10' 10'' and basal hub 30, 30', 30''can be designed to retain a pressurized volume of insulin that is sufficient for the patient to utilize during sleep of approximately 8 hours. The pressure element in the infusion set 10, 10', 10'' (e.g. a compression spring 36) can be preloaded or charged using the pressure of the infusion pump, in combination with a separate septum or check valve (not shown) in the infusion base 10, 10', 10''. In this case, a connection port is provided in the basal hub and the user attaches the line set hub or connector to the connection port to redirect the insulin flow internal to the hub 22, allowing the nighttime reservoir to fill. Once the connection is made, the user implements a command from the infusion pump controller to fill the flexible reservoir 34, 140, 140' with the total dose for nighttime basal delivery. The user then disconnects the line set hub or connector from the hub 22. The basal hub 30 can be modified to be filled from the line set whereupon the line set is disconnected, or the infusion set hub can be modified to incorporate a basal reservoir which is filled using the pump at nighttime before the line set is disconnected.

The line set hub of a conventional infusion set can also be redesigned to incorporate the basal reservoir 34, 140, 140' to retain a pressurized volume of insulin that is sufficient for the patient to utilize during sleep of approximately 8 hours. The pressure element in the infusion set 10, 10', 10" (e.g. a compression spring 36) can be preloaded or charged using the pressure of the infusion pump, in combination with a two-position valve (not shown) in the line set hub. In this case, the user shifts the two-position valve to redirect the insulin flow internal to the line set hub, allowing the nighttime reservoir to fill. Once the valve is shifted, the user implements a command from the infusion pump controller to fill the flexible reservoir 34, 140, 140' with the total dose for nighttime basal delivery. The user then disconnects the line set 20 from the hub 22 and shifts the two-position valve back to the original setting. The flow of insulin from the basal reservoir 34, 140, 140' passes through a reduced orifice to the infusion cannula 15 so that the basal infusion is restricted and maintained at a predetermined rate.

The use of a flexible reservoir or bladder 34, a compression spring 36 preloaded to exert a force on the bladder 34, and a flow cannula 16 with a specified diameter and length, can provide a predetermined and relatively constant flow rate of insulin or other medication to be released from the basal hub 30. Similarly, for the basal hub 30', 30", the amount of pressure in the fluid reservoir 140, 140' can be regulated by the tension on the flexible membrane 120.

The flow cannula 16, 16', 16", as well as the infusion cannula 15, can be a one-piece injection molded unit formed of a polymer, or it can be made of steel or other metallic material. Upon connection of the basal hub 30, 30', 30" to an infusion base 10, 10', 10", an end of the flow cannula 16, 16', 16" penetrates the septum 38, 125 of the basal hub 30, 30', 30". The flow cannula 16, 16', 16" may be sharp or blunt. However, if it is blunt, the septum 38, 125 may need to be pre-slit or pre-pierced to accommodate such a blunt cannula. Upon awakening from sleep, the patient removes the basal hub 30, 30', 30" from the infusion base 10, 10', 10" and connects a line set 20, as illustrated in FIG. 5B, to the infusion base 10, 10', 10".

When basal infusion is not provided for a diabetic patient, blood glucose level will rise, on average, by one (1) mg/dl for each minute that an infusion set is not connected. During sleep, a number of problems may occur, e.g. the infusion line or tube set may become kinked or pinched, or the line set may disconnect from the infusion base, all of which may result in the patient's blood glucose level increasing over time, potentially causing serious harm to the patient. Thus it is essential for the diabetic patient to reliably receive basal infusion during rest periods or when the patient is disconnected from the infusion pump for extended periods. The disclosed embodiments of the present invention meet this need.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

What is claimed is:

1. A method of administering liquid medication to a patient, comprising:
   during a first period of time, administering liquid medication to the patient only from a remote infusion pump through an extension set attached to an infusion base that is attached to the patient; and
   during a second period of time, administering liquid medication to the patient only from a reservoir pressurized by a preloaded compression element and contained in a basal hub attached directly to the infusion base in a manner preventing the simultaneous attachment of an extension set to the infusion base.

2. The method as claimed in claim 1, wherein the extension set comprises a set hub and a tube set, the tube set being connected to the set hub and the pump to deliver liquid medication from the pump into an infusion cannula of the set hub.

3. The method as claimed in claim 1, wherein the basal hub delivers liquid medication from the reservoir into an infusion cannula of the infusion base.

4. The method as claimed in claim 1, wherein the first period of time is a waking period and the second period of time is a sleeping or resting period.

5. The method as claimed in claim 1, wherein the first period of time is a daytime period and the second period of time is a nighttime period.

6. The method as claimed in claim 1, wherein the basal hub is configured to deliver a basal dose of liquid medication during periods of inactivity.

7. The method as claimed in claim 1, wherein liquid medication comprises insulin.

8. The method as claimed in claim 1, wherein the preloaded compression element comprises a spring or a membrane.

9. A method of administering liquid medication to a patient, comprising:
   during a first period of time, administering liquid medication to the patient from a remote infusion pump through an extension set to an infusion base that is attached to the patient;
   detaching the extension set from the infusion base;
   during a second period of time, administering liquid medication to the patient from a reservoir in a basal hub attached to the infusion base; and
   after the step of detaching the extension set from the infusion base and before the second period of time, implementing a command from an infusion pump controller to fill the reservoir of the basal hub with a quantity of liquid medication required for a basal dose, and recording the basal dose as a bolus dose by the infusion pump.

10. A method of administering liquid medication to a patient, comprising:
    during a first period of time, administering liquid medication to the patient from a remote infusion pump through an extension set to an infusion base that is attached to the patient;
    detaching the extension set from the infusion base;
    during a second period of time, administering liquid medication to the patient from a reservoir in a basal hub attached to the infusion base;
    after the step of detaching the extension set from the infusion base and before the second period of time, implementing a command from an infusion pump controller to fill the reservoir of the basal hub with a quantity of liquid medication required for a basal dose; and
    capturing a total dose delivered during a period of sleep or inactivity as part of a total daily dose.

* * * * *